(12) United States Patent
Rule et al.

(10) Patent No.: US 10,888,463 B2
(45) Date of Patent: Jan. 12, 2021

(54) VISCOELASTIC MEDICAL ARTICLE

(71) Applicant: 3M INNOVATIVE PROPERTIES COMPANY, Saint Paul, MN (US)

(72) Inventors: Joseph D. Rule, Cottage Grove, MN (US); Naimul Karim, Maplewood, MN (US); John J. Rogers, Saint Paul, MN (US); Guido Hitschmann, Neuss (DE)

(73) Assignee: 3M INNOVATIVE PROPERTIES COMPANY, St. Paul, MN (US)

( * ) Notice: Subject to any disclaimer, the term of this patent is extended or adjusted under 35 U.S.C. 154(b) by 1242 days.

(21) Appl. No.: 15/103,898

(22) PCT Filed: Dec. 9, 2014

(86) PCT No.: PCT/US2014/069209
§ 371 (c)(1),
(2) Date: Jun. 13, 2016

(87) PCT Pub. No.: WO2015/094792
PCT Pub. Date: Jun. 25, 2015

(65) Prior Publication Data
US 2016/0310327 A1    Oct. 27, 2016

Related U.S. Application Data

(60) Provisional application No. 61/918,167, filed on Dec. 19, 2013.

(51) Int. Cl.
*A61F 13/02*    (2006.01)
*A61F 13/00*    (2006.01)
*A61F 13/08*    (2006.01)

(52) U.S. Cl.
CPC .... *A61F 13/0273* (2013.01); *A61F 13/00029* (2013.01); *A61F 13/00038* (2013.01); *A61F 13/08* (2013.01)

(58) Field of Classification Search
CPC combination set(s) only.
See application file for complete search history.

(56) References Cited

U.S. PATENT DOCUMENTS

| | | |
|---|---|---|
| 2,740,402 A | 4/1956 | Scholl |
| 3,575,782 A | 4/1971 | Hansen |
| (Continued) | | |

FOREIGN PATENT DOCUMENTS

| | | |
|---|---|---|
| CN | 1248302 | 3/2000 |
| CN | 1341052 | 3/2002 |
| (Continued) | | |

OTHER PUBLICATIONS

Ahmad, "Feasibility study of polyurethane shape-memory polymer actuators for pressure bandage application"; Sci. Technol. Adv. Mater., 2012, vol. 13, 015006, 7pages.

(Continued)

*Primary Examiner* — Ophelia A Hawthorne
(74) *Attorney, Agent, or Firm* — 3M IPC (57) ABSTRACT

A medical article and methods of using same. The medical article can include a machine direction (MD) and a cross-machine direction (CMD); a support layer; and a viscoelastic layer. The viscoelastic layer can be coupled to the support layer, and the viscoelastic layer can be discontinuous in the MD and/or the CMD. The viscoelastic layer can recover at least 70% of its deformation after 48 hours at room temperature after being strained to 50% elongation, such that the medical article has a first tensile stiffness $T_1$ at a first strain rate $S_1$, and a second tensile stiffness $T_1$ at a second strain rate $S_1$. The ratio of $S_1/S_2$ can be at least 100, and the ratio of $T_1/T_2$ can be at least 1.5. The method can include wrapping the medical article around a body part; applying the first strain rate $S_1$; and applying the second strain rate $S_2$.

23 Claims, 4 Drawing Sheets

(56) References Cited

U.S. PATENT DOCUMENTS

| | | | |
|---|---|---|---|
| 4,414,970 A | 11/1983 | Berry | |
| 4,984,584 A | 1/1991 | Hansen | |
| 4,984,585 A | 1/1991 | Austad | |
| 5,209,801 A * | 5/1993 | Smith | A41D 20/00 156/161 |
| 7,361,241 B2 | 4/2008 | Barth | |
| 7,854,716 B2 | 12/2010 | Schuren | |
| 7,854,717 B1 | 12/2010 | Lentz | |
| 2005/0025937 A1 | 2/2005 | Maki | |
| 2009/0082711 A1 | 3/2009 | Paasche | |
| 2010/0191163 A1 | 7/2010 | Dennis | |
| 2011/0045306 A1 | 2/2011 | Johnson | |
| 2011/0071448 A1 | 3/2011 | Margiotta | |
| 2013/0303957 A1 | 11/2013 | Bauerfeind | |

FOREIGN PATENT DOCUMENTS

| | | |
|---|---|---|
| CN | 1379799 | 11/2002 |
| CN | 2664629 Y | 12/2004 |
| EP | 0761188 | 3/1997 |
| EP | 1894551 | 3/2008 |
| EP | 2444040 | 4/2012 |
| JP | 57-066752 | 4/1982 |
| JP | 63-197454 | 8/1988 |
| JP | 2009-532071 | 9/2009 |
| WO | WO 98/37266 | 8/1998 |
| WO | WO 00/44556 | 8/2000 |
| WO | WO 01/19920 | 3/2001 |
| WO | WO 2006/110527 | 10/2006 |
| WO | WO 2012-158879 | 11/2012 |

OTHER PUBLICATIONS

Kumar, "Prediction of internal pressure profile of compression bandages using stress relaxation parameters"; Biorheology, 2012, vol. 49, 13 pages.

Prieb, "Compression bandages and pressure gradient systems on the basis of TiNi Shape Memory Alloys in the Medical Field", Presentation for European symposium (Euromat '97, Maastricht—NL, Apr. 21-23, 1997) 6 pages.

Steckmann, "Compression bandages and gradient systems on the basis of TiNi shape memory alloys in the field of medicine"; 1$^{st}$ Memory Alloys GmbH, 5 pages.

International Search report for PCT International Application No. PCT/US2014/069209 dated Mar. 19, 2015, 4 pages.

* cited by examiner

VISCOELASTIC MEDICAL ARTICLE

CROSS REFERENCE TO RELATED APPLICATIONS

This is a national stage filing under 35 U.S.C. § 371 of PCT Application No. PCT/US2014/069209, filed Dec. 9, 2014, which claims the benefit of U.S. Provisional Application No. 61/918,167, filed Dec. 19, 2013, the disclosures of which are incorporated herein by reference in their entirety.

FIELD

The present disclosure generally relates to viscoelastic medical articles and methods of using same. Particularly, the present disclosure relates to viscoelastic compression bandages.

BACKGROUND

Compression bandages are known for use in the treatment of edema, as well as venous and lymphatic disorders, e.g., of the lower limbs. Areas where compression bandages are considered particularly useful are the management and treatment of chronic wounds, such as venous leg ulcers.

Compression bandages are one of the common compression systems used for compression therapy. The use of such compression bandages generally involves the application of a multilayer compression bandage. One concept behind a number of such multi-layer bandaging systems is the use of a combination of different types of bandage layers in order to apply pressure in layers (giving an accumulation of pressure) and to provide sustained compression together with rigidity. Commercially available compression bandages include bandages marketed under the trade designations "3M COBAN 2" and "3M COBAN 2 LITE". Typically, to assure proper and effective compression bandaging, it is normally necessary for a medical professional to apply the bandages. In the start of treatment of lymphedema or in other compression therapies where edema is present, compression bandages generally need to be replaced frequently due to changes in pressure (e.g. reduction of pressure) and/or in uniformity of pressure of the compression bandage. As the amount of edema is reduced during compression therapy, the need of having a skilled medical professional change and reapply the compression bandage to ensure the desired pressure profile for continuing compression treatment can be limiting.

SUMMARY

The present disclosure is generally directed to medical articles having a machine direction (MD) and a cross-machine direction (CMD) comprising a support layer and a viscoelastic layer coupled to the support layer, where the viscoelastic layer is discontinuous in at least one of the MD and the CMD. The medical articles can include, or be employed in, compression bandages or devices. Such compression bandages can be used in compression therapy for applying compression to a body part (e.g. a limb, torso, head, neck, or a combination thereof) of a subject for the use in the treatment and/or management of edema and other venous and lymphatic disorders of a body part (e.g. limb, torso, neck and/or head), more particularly venous leg ulcers and lymphedema of a limb.

Within a broad range of stretch ratios, medical articles of the present disclosure generally exhibit a rigid (e.g., non-compliant) character or behavior in response to fast deformations, and a compliant character or behavior in response to slow deformations, thereby exhibiting a strain-rate-dependent behavior.

Some aspects of the present disclosure provide a medical article. The medical article can include a machine direction (MD) and a cross-machine direction (CMD); a support layer; and a viscoelastic layer. The viscoelastic layer can be coupled to the support layer, and the viscoelastic layer can be discontinuous in at least one of the MD and the CMD. The viscoelastic layer can recover, in at least one of the MD and the CMD, at least 70% of its deformation after 48 hours at room temperature after being strained to 50% elongation, such that the medical article has, at room temperature, in at least one of the MD and the CMD, a first tensile stiffness $T_1$ at a first strain rate $S_1$ applied in the at least one of the MD and the CMD and a second tensile stiffness $T_2$ at a second strain rate $S_2$ applied in the at least one of the MD and the CMD. The ratio of $S_1/S_2$ can be at least 100, and the ratio of $T_1/T_2$ can be at least 1.5.

Some aspects of the present disclosure provide a method of using a medical article. The method can include providing a medical article. The medical article can include a machine direction (MD) and a cross-machine direction (CMD); a support layer; and a viscoelastic layer. The viscoelastic layer can be coupled to the support layer, and the viscoelastic layer can be discontinuous in at least one of the MD and the CMD. The viscoelastic layer can recover, in at least one of the MD and the CMD, at least 70% of its deformation after 48 hours at room temperature after being strained to 50% elongation. The method can further include wrapping the medical article around a body part of a subject, such that at least one of the MD and the CMD extends around the body part. The method can further include applying a first strain rate $S_1$ in at least one of the MD and the CMD to the medical article wrapped on the body part, wherein the medical article exhibits a first tensile stiffness $T_1$ at the first strain rate $S_1$; and applying a second strain rate $S_2$ in at least one of the MD and the CMD to the medical article wrapped on the body part, wherein the medical article exhibits a second tensile stiffness $T_2$ at the second strain rate $S_2$. The ratio of $S_1/S_2$ can be at least 100, and the ratio of $T_1/T_2$ can be at least 1.5.

Other features and aspects of the present disclosure will become apparent by consideration of the detailed description and accompanying drawings.

DETAILED DESCRIPTION

Before any embodiments of the present disclosure are explained in detail, it is to be understood that the invention is not limited in its application to the details of construction and the arrangement of components set forth in the following description or illustrated in the following drawings. The invention is capable of other embodiments and of being practiced or of being carried out in various ways. Also, it is to be understood that the phraseology and terminology used herein is for the purpose of description and should not be regarded as limiting. The use of "including," "comprising," or "having" and variations thereof herein is meant to encompass the items listed thereafter and equivalents thereof as well as additional items. Unless specified or limited otherwise, the terms "affixed," and "coupled" and variations thereof are used broadly and encompass both direct and indirect affixations and couplings. It is to be understood that other embodiments may be utilized, and structural or logical changes may be made without departing from the scope of the present disclosure.

The present disclosure generally relates to medical articles that include a viscoelastic layer that allows the resulting medical article to exhibit a more rigid, stiff, or less compliant behavior in response to higher (i.e., faster) strain rates and a softer, more compliant behavior in response to lower (i.e., slower) strain rates. Examples of higher strain rates may occur, for example, when a subject is walking, running, when stresses are being applied by a therapeutic device, or higher strain rates are otherwise being produced on the medical article. Lower strain rates may occur, for example, as a result of allowing the subject to stand (e.g., if the medical article is wrapped around the lower leg), to sit (e.g., if the medical article is wrapped around a knee that is bent in the sitting position), to have deswelling (or decreasing edema), or otherwise produce a lower strain rate on the medical article.

As mentioned above, medical articles of the present disclosure can include, or be employed in, compression devices, such as compression bandages, wraps, dressings, or the like. A particularly useful compression device of the present disclosure would meet the following criteria related to its force-elongation behavior in the applied state: (i) the device generally acts as a relatively rigid (e.g., non-stretchable) sleeve to enable the muscle pump mechanism; and (ii) the device is generally tight enough to stay in place on a body part, but not so tight that it is uncomfortable or even unsafe to wear for extended periods.

Conventional compression devices (e.g., bandages) can generally meet both of these criteria through a non-linear force-elongation behavior upon stretching, as long as the bandage is applied at "full stretch", i.e. the degree of elongation that is the transition between an elastic, low modulus section and a high modulus section. The high modulus section can be determined by the stress-strain properties of a support layer (e.g., a non-woven) employed in the device. In cases where such devices are applied with too little stretch (or in cases of edema volume loss, which can occur, for example, within in the first few hours of the application), the compression provided by the device might be too low to adequately meet the compression needs.

In contrast, medical articles (e.g., compression bandages) of the present disclosure can provide similar proper compression therapy behavior, but at a relatively broad range of stretch ratios, where the ratio of stretched length to relaxed length is referred to as stretch ratio. As a result, medical articles, and particularly compression bandages, of the present disclosure can enable extended compression therapy on edemas that are rapidly decreasing in size. In addition, medical articles of the present disclosure can enable less-skilled caregivers to safely and effectively apply the medical articles because, compared to existing medical articles, the compressive force exerted by the medical articles of the present disclosure is less dependent on stretch ratio.

That is, medical articles of the present disclosure have a unique performance due to the viscoelastic layer employed in the medical articles. The viscous nature of the viscoelastic layer generally refers to their increasing resistance to elongation when they are stretched at increasing speeds. The elastic nature of the viscoelastic layer generally refers to their ability to spontaneously recover their original length after being elongated. As a result, the viscoelastic layer, or the materials making up the viscoelastic layer generally function as viscoelastic solids, rather than viscoelastic liquids. The overall effect is that the viscoelastic layer can be stretched like other elastomers, but the force required to stretch the strand depends on both how fast the viscoelastic layer is being stretched and how far it has been stretched. This is different from elastic materials used in conventional compression bandages in which the force required to stretch the elastic material varies with how far the elastic material is stretched, but varies relatively little, or not at all, with how fast the material is stretched.

The present inventors recognized that, in a compression therapy application, muscle contractions (amplitudes) that enable the muscle pump mechanism happen relatively rapidly, causing relatively high strain rates in a compression device employed. The present inventors further recognized that, in contrast, conformability to a limb, potential sloughing of the compression device (e.g., bandage), and deswelling all happen relatively slowly, causing relatively low strain rates in the compression device employed. As a result, the present inventors discovered that medical articles (e.g., compression bandages) that employ a viscoelastic layer of the present disclosure could exhibit a desirable, more rigid behavior in response to higher strain rates, while also exhibiting a desirable, more compliant behavior in response to lower strain rates.

Figure 1:
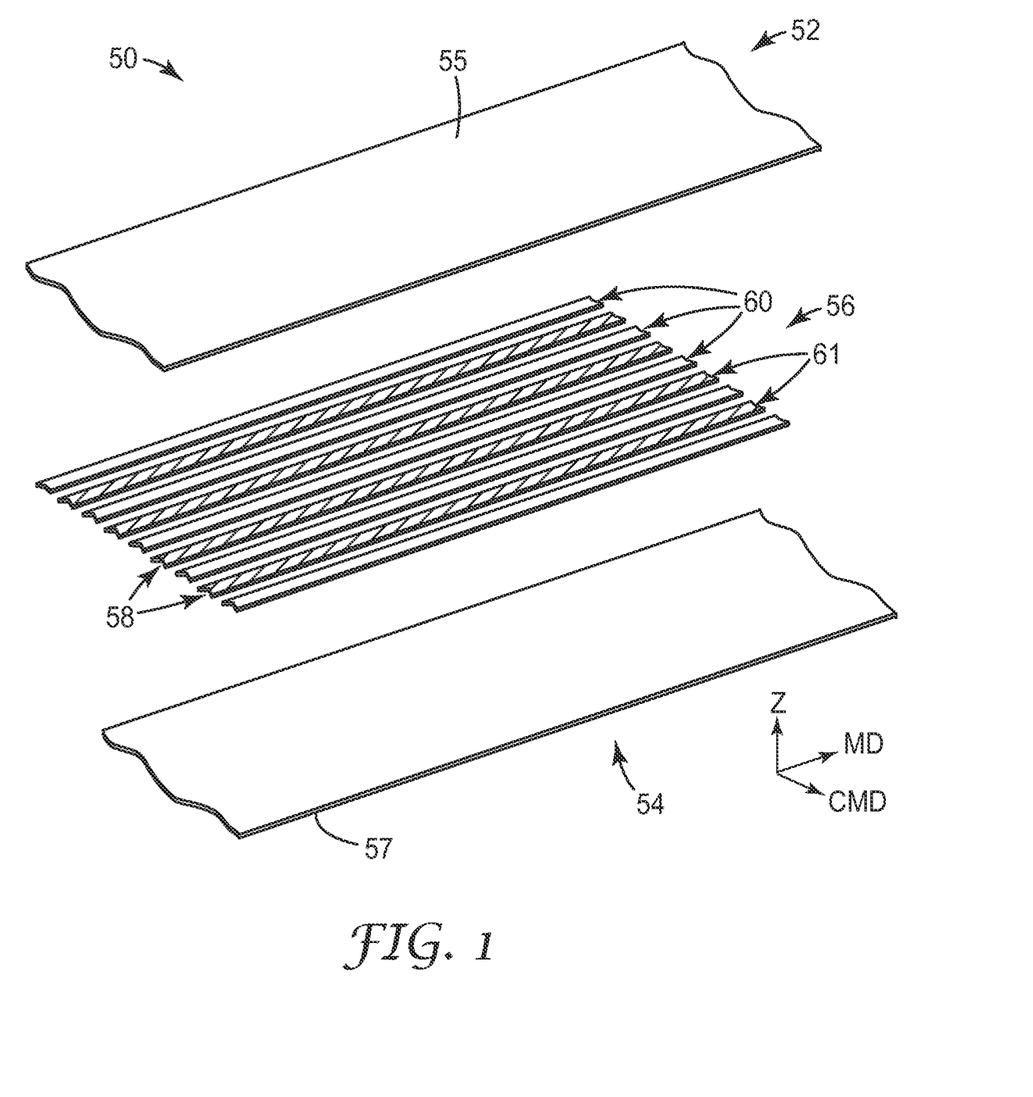
FIG. 1 is an exploded schematic perspective view of a medical article according to one embodiment of the present disclosure, the medical article comprising a viscoelastic layer.

FIG. 1 illustrates a medical article 50 according to one embodiment of the present disclosure. The medical article 50 includes a first support layer 52, a second support layer 54, and a viscoelastic layer 56 located between the first support layer 52 and the second support layer 54. The viscoelastic layer 56 can be coupled (e.g., bonded) to at least one of the first support layer 52 and the second support layer 54. The medical article 50 of FIG. 1 is illustrated as including two support layers 52, 54, however, it should be understood that in some embodiments, the medical article 50 can include only one of the support layers 52, 54.

The medical article 50 can include a machine (or longitudinal) direction (MD) and a cross-machine (or transverse) direction (CMD), as shown in FIG. 1. As shown in FIG. 1, the viscoelastic layer 56 can be discontinuous in at least one of the MD and the CMD, such that the viscoelastic layer 56 includes at least one opening 58 in a z-direction (see FIG. 1—i.e., orthogonal to the plane of the medical article 50 and oriented substantially perpendicularly with respect to the MD and the CMD). Such a configuration can allow the first support layer 52 and the second support layer 54 to be coupled (e.g., bonded) to one another across or through the viscoelastic layer 56, i.e., in the region of the one or more openings 58.

Preferably, the viscoelastic layer 56 has at least one continuous portion in the MD, while still being generally discontinuous. The term "discontinuous" generally refers to the viscoelastic layer being incompletely continuous such that the layer includes voids, openings, cutaway regions, or regions of discontinuity in the MD and/or the CMD, and these regions of discontinuity extend through the entire Z-direction of the viscoelastic layer 56. The discontinuities are such that a line can be drawn across the viscoelastic layer 56 in the MD and/or the CMD that overlaps at least one of these regions of discontinuity. The viscoelastic layer 56 of FIG. 1 also includes discrete elements (strands, as described below); however, as will be described in greater detail below with respect to FIGS. 2 and 3, "discontinuous" does not mean that the viscoelastic layers of the present disclosure necessarily include such discrete disconnected elements, and rather, a discontinuous viscoelastic layer of the present disclosure can include a continuous portion (e.g., a connected lattice network or configuration) while also being "discontinuous" for purposes of the present disclosure. These discontinuities can be advantageous in allowing the transmission of air and moisture through the medical article, e.g., to help prevent skin masceration when employed.

The viscoelastic layer 56 can be substantially coextensive with the support layers 52, 54 in at least the MD. In some embodiments, as shown in FIG. 1, the viscoelastic layer 56 can also be substantially coextensive with the support layers 52, 54 in the CMD, with the exception of the opening(s) 58. That is, the total area occupied by the viscoelastic layer 56, including the opening(s) 58 can be substantially equal to the area of the support layers 52, 54.

Figure 2:
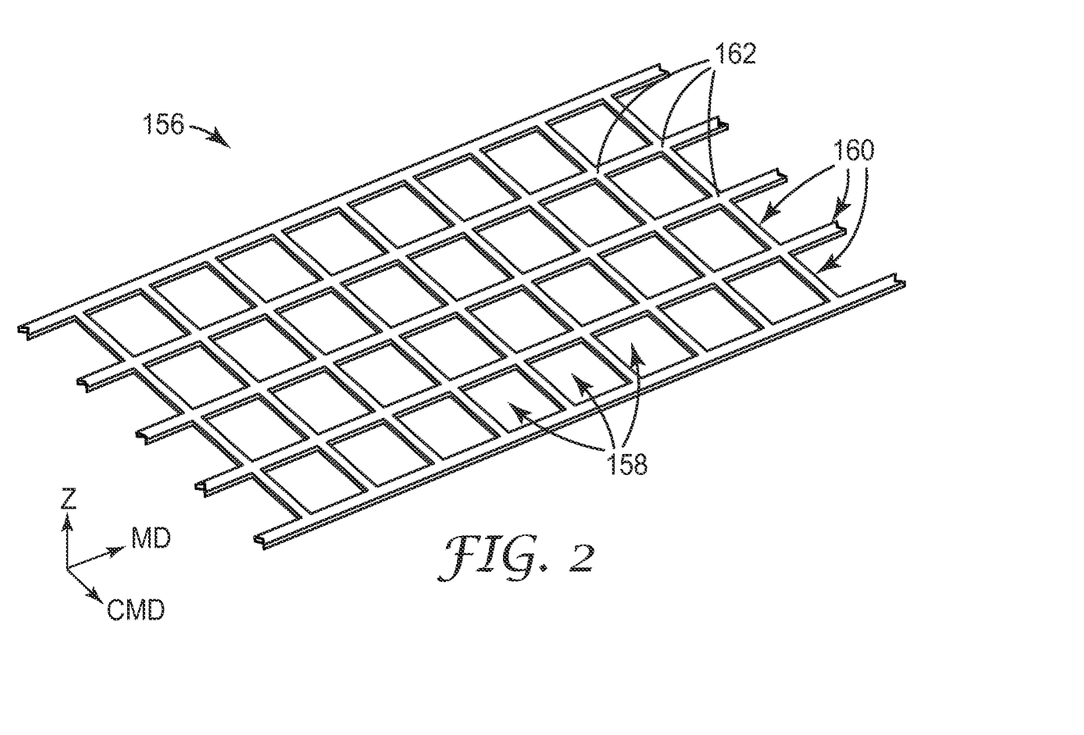
FIG. 2 is a schematic perspective view of a viscoelastic layer according to another embodiment of the present disclosure.
Figure 3:
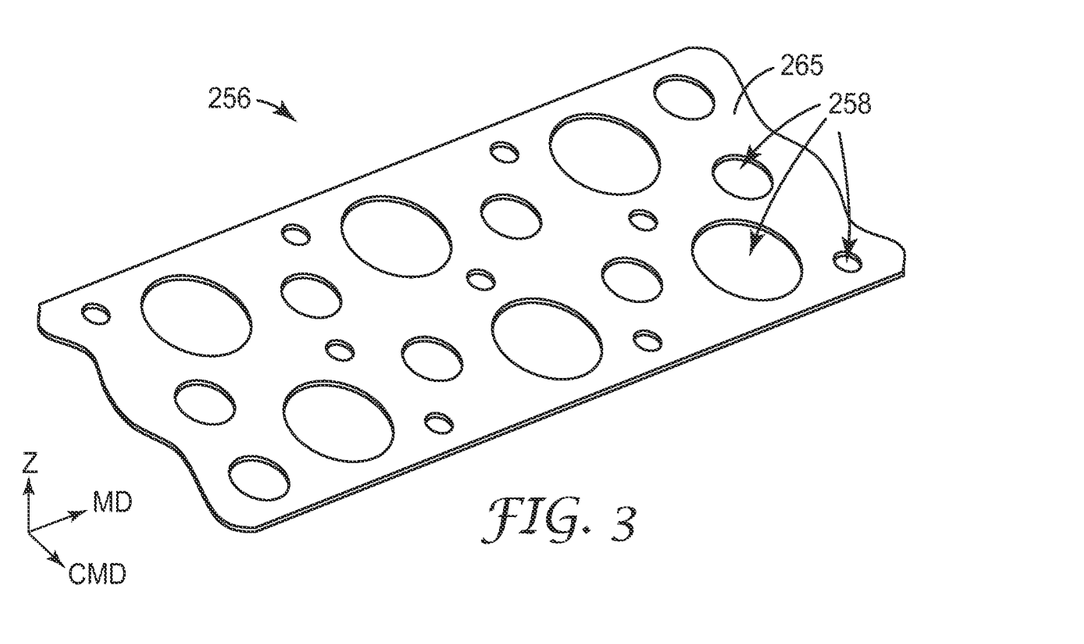
FIG. 3 is a schematic perspective view of a viscoelastic layer according to another embodiment of the present disclosure.

The viscoelastic layer 56 of FIG. 1 is illustrated by way of example only as including a plurality of individual, substantially parallel viscoelastic elements, such as the strands 60 shown in FIG. 1, that extend in the MD and are spaced apart in the CMD, such that the viscoelastic layer 56 of FIG. 1 is continuous in the MD and discontinuous in the CMD. In some embodiments, the strands 60 can be equally spaced apart in the CMD or can be spaced apart varying distances, such that the resulting openings 58 can be uniform in size (i.e., width, in the CMD), or varying in size. In contrast to foam, in which openings are defined by a tortuous path, the openings 58 are non-tortuous and extend straight through the viscoelastic layer 56 (i.e., through the viscoelastic layer 56 in the z-direction, or in a direction substantially orthogonal to the MD and the CMD). Each strand 60 can be coupled (e.g., bonded) to at least one of the first support layer 52 and the second support layer 54. Other configurations of discontinuous viscoelastic layers of the present disclosure are possible, and additional examples are illustrated in FIGS. 2 and 3 and described below.

The viscoelastic layer 56 is relatively thin, i.e., in the z-direction. That is, the viscoelastic layer 56 can include a sheet or film configuration and can be substantially solid, such that the viscoelastic layer 56 is not a foam having a substantial z-direction thickness and generally excludes air. Said another way, the viscoelastic layer 56 can generally be denser than a foam and less compressible than a foam. Furthermore, the viscoelastic layer 56 can include a first dimension in the MD, a second dimension in the CMD, and a third dimension in the z-direction that is no greater than (or less than) 1% (or 0.01) of the first dimension and/or the second dimension; in some embodiments, no greater than (or less than) 0.5% (or 0.005) of the first dimension and/or the second dimension; in some embodiments; and in some embodiments, no greater than 0.1% (or 0.001) of the first dimension and/or the second dimension; in some embodiments.

In some embodiments, the viscoelastic layer 56 (e.g., the strands 60) can be stretched (e.g., to 25% elongation) in the MD and/or the CMD, and in this stretched configuration, can be coupled (e.g., bonded) to the first support layer 52 and/or the second support layer 54, as described in U.S. Pat. No. 3,575,782, which is incorporated herein by reference. The resulting laminate can subsequently be impregnated and/or coated to form a self-adhering device (e.g., bandage). As a result, in some embodiments, the medical article 50 can form at least a portion of a self-adhering bandage. In embodiments in which the viscoelastic layer 56 is pre-stretched prior to being coupled to the first support layer 52 and/or the second support layer 54, the first support layer 52 and/or the second support layer 54 may have an at least slightly puckered appearance when the tension on the viscoelastic layer 56 is released.

Extent of compression provided can be related to, inter alia, the size of the strands 60 and/or the number of strands 60 employed, whereby increased compression can generally result from using a greater number of larger strands 60 in the medical article 50. Suitably, the number of strands 60 per inch (epi) may range from about 4 to about 25 epi, while the strands may have a denier ranging from about 200 to about 1700. For use in medical articles 50 of the present disclosure, particularly for treatment and/or management of venous leg ulceration, it has been found that the use of from about 10 to about 20 epi together with a strand denier of about 650 or less (more favorably about 620 or less, most favorably about 580 or less) can be beneficial in providing desirable ease in handling of the medical article itself as well as desired therapeutic compressive force without observation of undesirably high resting pressures. Within the mentioned denier range, a suitable minimal denier for effective desired therapeutic compressive force may be at least about 350 denier (more favorably at least about 425 denier, and most favorably at least about 500 denier).

In some embodiments, the epi can be no greater than 15, in some embodiments, no greater than 12, and in some embodiments, no greater than 10. In some embodiments, the epi can be at least 4, in some embodiments, at least 5, and in some embodiments, at least 6. In some embodiments, the strands 60 can have a denier of no greater than 550, in some embodiments, no greater than 450, and in some embodiments, no greater than 350. In some embodiments, the strands 60 can have a denier of at least 100, in some embodiments, at least 150, and in some embodiments, at least 200.

The viscoelastic layer 56 can be coupled to one or both support layers 52, 54 and/or the support layers 52, 54 can be coupled together by a variety of coupling means, including, but not limited to, adhesive bonding and/or mechanical bonding. Examples of mechanical bonding can include, but are not limited to, hydroentangling, stitching, knitting, needling, or combinations thereof.

The viscoelastic layer 56 recovers elastically after it is deformed by elongation from its fully relaxed state. The fully relaxed state can be reached by raising the viscoelastic layer to a temperature of at least 40° C. in the absence of constraint or applied force. After the viscoelastic layer is strained to 50% elongation, it can be characterized by recovering, in at least one of the MD and CMD, at least 70% of its deformation after 48 hours at room temperature. In other words, after recovering 70% of its original 50% elongation, the overall elongation of the viscoelastic layer 56 would be 15% elongation. In some embodiments, the viscoelastic layer 56 can recover at least 75% of its deformation; in some embodiments, at least 80% of its deformation; in some embodiments, at least 90% of its deformation; in some embodiments, at least 95% of its deformation; and in some embodiments, 100% of its deformation, with room temperature being generally 22-27° C.

In some embodiments, the viscoelastic layer 56 can be further characterized by recovering, in at least one of the MD and the CMD, at least 20% of its deformation after 30 minutes at room temperature after being strained to 50% elongation; in some embodiments, at least 30% of its deformation; in some embodiments, at least 40% of its deformation; in some embodiments, at least 50% of its deformation; and in some embodiments, at least 60% of its deformation.

In some embodiments, the viscoelastic layer 56 can be further characterized by having, at room temperature, in at least one of the MD and the CMD, a first tensile stiffness $T_1$ at a first (i.e., higher) strain rate $S_1$ applied in at least one of the MD and the CMD and a second tensile stiffness $T_2$ at a second (i.e., lower) strain rate $S_2$ applied in at least one of the MD and the CMD, wherein the ratio of $S_1/S_2$ is at least 100 (in some embodiments, at least 150, and in some embodiments, at least 200), and wherein the ratio of $T_1/T_2$ is at least 1.5. In some embodiments, the ratio of $T_1/T_2$ can be at least 2; in some embodiments, at least 2.5; in some embodiments, at least 3; in some embodiments, at least 3.5; in some embodiments, at least 4; in some embodiments, at least 4.5; and in some embodiments, at least 5. In some embodiments, the ratio of $T_1/T_2$ can be no greater than 10; in some embodiments, no greater than 9; in some embodiments, no greater than 8; in some embodiments, no greater than 7; and in some embodiments, no greater than 6.

As a result, the medical article 50 comprising the viscoelastic layer 56 can be characterized by recovering, in at least one of the MD and the CMD, at least 70% of its deformation after 48 hours at room temperature after being strained to at least 25% elongation, and in some embodiments, at least 50% elongation (in at least one of the MD and CMD, respectively); in some embodiments, at least 75% of its deformation; in some embodiments, at least 80% of its deformation; in some embodiments, at least 90% of its deformation; in some embodiments, at least 95% of its deformation; in some embodiments, at least 97% of its deformation; in some embodiments, at least 98% of its deformation; and in some embodiments, at least 99% of its deformation.

In some embodiments, the medical article 50 can be further characterized by recovering, in at least one of the MD and the CMD, at least 20% of its deformation after 30 minutes at room temperature after being strained to 50% elongation; in some embodiments, at least 30% of its deformation; in some embodiments, at least 40% of its deformation; in some embodiments, at least 50% of its deformation; and in some embodiments, at least 60% of its deformation.

In some embodiments, the medical article 50 can be further characterized by having, at room temperature, in at least one of the MD and the CMD, a first tensile stiffness $T_1$ at a first (i.e., higher) strain rate $S_1$ applied in at least one of the MD and the CMD and a second tensile stiffness $T_2$ at a second (i.e., lower) strain rate $S_2$ applied in at least one of the MD and the CMD, wherein the ratio of $S_1/S_2$ is at least 100 (in some embodiments, at least 150, and in some embodiments, at least 200), and wherein the ratio of $T_1/T_2$ is at least 1.5. In some embodiments, the ratio of $T_1/T_2$ can be at least 2; in some embodiments, at least 2.5; in some embodiments, at least 3; in some embodiments, at least 3.5; in some embodiments, at least 4; in some embodiments, at least 4.5; and in some embodiments, at least 5.

In some embodiments, the first strain rate $S_1$ can be no greater than about 500 cm/min.; in some embodiments, no greater than 100 cm/min.; and in some embodiments, no greater than 50 cm/min. In some embodiments, the second strain rate $S_2$ can be at least about 0.01 cm/min.; in some embodiments, at least 0.1 cm/min.; and in some embodiments, at least 0.5 cm/min.

The above properties generally provide a medical article that has the desired stretchability, while also having the desired conformability and strain-rate-dependent behavior described above, particularly, in the MD and/or the CMD. Some viscoelastic foams have been employed in conventional bandages or wraps in order to provide comfort and conformability in a z-direction, such that the overall compressive force of the bandage in the z-direction is maintained. The compressibility of these foams allows them to conform to a surface without requiring deformation in the MD and/or the CMD. However, the viscoelastic layers of the present disclosure are generally not compressible, so they can conform to a surface only with deformations in the MD and/or the CMD. This enhanced role of the elastic and viscous behavior in the MD and/or the CMD leads to the unique strain-rate-dependent properties described above including rigidity in response to fast deformations.

In some embodiments, at least one of the support layers 52, 54 can function to provide a deadstop or stretch limit for the viscoelastic layer 56, such that one or both of the support layers 52, 54 can prevent over stretching of the medical article (and the viscoelastic layer 56) and can inhibit the viscoelastic layer 56 can fracturing, e.g., under high amounts of elongation.

The viscoelastic layer 56 can be formed of a variety of materials that meet the limitations of the present disclosure, including, but not limited to, polyurethanes, polyureas, polyethers, polyesters, poly (meth)acrylates, polyolefins, polyvinyl chloride, and combinations thereof.

The support layers (e.g., the first support layer 52 and/or the second support layer 54) of the present disclosure can be formed of a variety of materials, including, but not limited to, woven, knitted, warp-knit, or nonwoven fibrous webs, foams, with woven and nonwoven fibrous webs being more suitable, and nonwoven fibrous webs being most suitable in terms of providing a favorably thin support layer, especially in its extended state. The first support layer 52 and the second support layer can be formed of the same or a different material.

As mentioned above, the medical article 50 (or a portion thereof, such as the first support layer 52 or the second support layer 54, or a surface or portion thereof) can be self-adhering, or form at least a portion of, a self-adhering device (e.g., bandage). For example, in some embodiments, only an outer facing surface 55 of the first support layer 52 and an outer facing surface 57 of the second support layer 54 (i.e., that make up the outer facing surfaces of the medical article 50) are self-adhering. In some embodiments, it can be preferred that the medical article 50 be configured not to adhere to clothing, hair or skin.

Examples of suitable types of self-adherent materials as well as methods of making such materials are disclosed in U.S. Pat. Nos. 3,575,782; 4,984,584; and US Patent Application No. 2005/0025937, which are incorporated herein by reference in their entirety. Other examples of suitable types of self-adherent materials include knitted and woven bandages commercially available under the trade designations ROSIDAL HAFT (Lohman & Rauscher GmbH & Co. KG, Neuwied Germany) and ACTICO (Activa Health Care, Burton-upon-Trent, UK).

The medical article 50 can further include a polymeric binder. For example, one or both of the first support layer 52 and the second support layer 54 can be coated or impregnated with a polymeric binder. In some embodiments, the strands 60 of the viscoelastic layer 56 can be bound to one or both of the first and second support layers 52 and 54 with a polymeric binder. In some embodiments, the polymeric binder is cohesive, so that the resulting medical article 50 is self-adherent (e.g., without adhering to clothing, hair or skin). Accordingly, at least one of the outer facing surfaces 55 and 57, and more suitably, both outer facing surfaces 55 and 57 comprise polymeric binder (e.g., such that the polymeric binder extends throughout the thickness of the medical article 50).

Suitable polymeric binders providing cohesive properties may be either elastomeric or non-elastomeric polymeric binders, however, preferably the polymeric binder is an elastomeric polymeric binder due to generally favorable properties of such binders, such as long-term flexibility, extensibility and/or elasticity. Suitable elastomeric polymeric binders may comprise natural rubber latex, a synthetic latex, such as homopolymer and copolymer latexes of acrylics, butadienes, styrene/butadiene rubbers, chloroprenes, ethylenes (e.g., vinyl acetate/ethylene), isoprenes, nitriles and urethanes, or mixtures thereof. Examples of suitable polymeric elastomeric binders are disclosed, for example, in U.S. Pat. Nos. 3,575,782 and 4,984,585. In some embodiments, the medical article 50 may be desirably free of natural rubber latex.

As mentioned above, the viscoelastic layer 56 can be partially extended (e.g., being maintained under partial tension) within the medical article 50. In order to provide preferred limited extensibility in the MD, during the manufacturing of such medical articles (e.g., during binding of the viscoelastic layer 56, e.g., with polymeric binder, to one or more support layers 52, 54) it can be preferable to stretch the viscoelastic layer 56 in the MD and/or the CMD to a length of at most 2.0, more preferably at most 1.75, even more preferable at most 1.5, most preferably about 1.5 times its fully relaxed length. The ratio of stretched length to relaxed length of the viscoelastic layer 56 is referred to as draw ratio. Generally a draw ratio of at least 1.2 to 1 is desirable.

As further shown in FIG. 1, in some embodiments, the medical article 50 can further include elastic materials or an elastic portion, e.g., as part of the viscoelastic layer 56 and/or as one or more separate elastic layers of the laminate medical article 50 (e.g., such that the elastic layer(s) are located at a different z-axis position than the viscoelastic layer 56). In some embodiments employing a separate elastic layer, the elastic layer can be located directly adjacent (e.g., on top off, underneath, or both) the viscoelastic layer 56. A medical article that includes an elastic portion as well as the viscoelastic layer 56 can have the advantage of providing immediate compression upon application of the medical article 50 (e.g., in a pre-stretched state) to a body part, thus holding the medical article 50 tight to the skin during the time necessary for the viscoelastic layer 56 to respond, i.e., to relax and compress.

Figure 4:
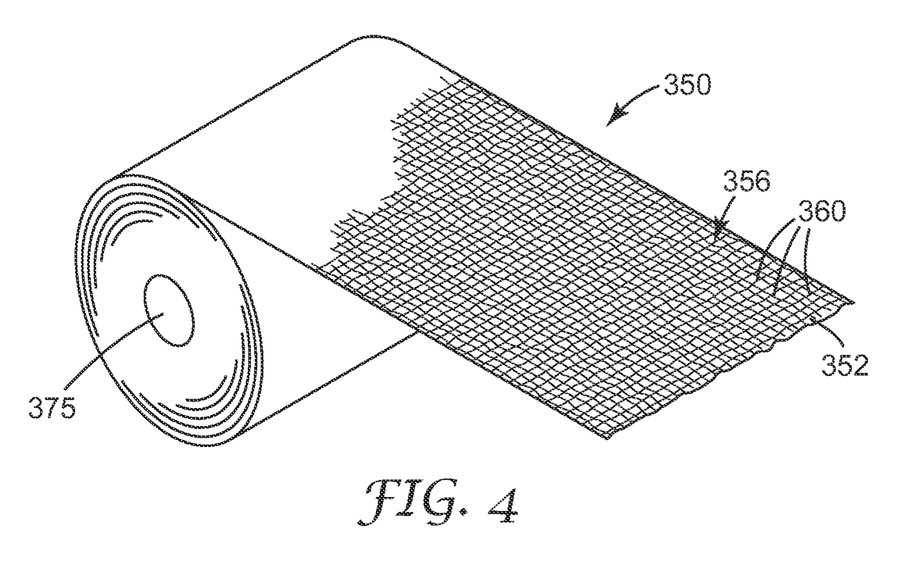
FIG. 4 is a perspective view of a medical article according to another embodiment of the present disclosure, the medical article shown in a rolled configuration.

By way of example only, the viscoelastic layer 56 of FIG. 1 is illustrated as including elastic elements, such as the strands 61 illustrated in FIG. 4, that intersperse the viscoelastic strands 60, i.e., such that one elastic strand 61 is located in each opening 58 defined between adjacent viscoelastic strands 60 and the elastic strands 61 and the viscoelastic strands 60 alternate in the layer 56. As a result of this exemplary arrangement, the elastic strands 61 can extend in the MD and be spaced apart in the CMD to also define openings therebetween that extend through the layer 56 in the z-direction. Such a configuration can allow the first and second support layers 52, 54 to still be coupled together across or through the layer 56.

As a result, in embodiments in which the elastic strands 61 are employed, the elastic portion of the medical article 50 can also be discontinuous. As shown, in some embodiments, the elastic portion (e.g., the elastic strands 61) of the medical article 50, if employed, can also be coextensive with the support layers 52, 54 in at least the MD. In some embodiments, the elastic portion can also be substantially coextensive with the support layers 52, 54 in the CMD, with the exception of any openings that may be present therein. That is, in some embodiments, the total area occupied by the elastic portion, including any openings therein, can be substantially equal to the area of the support layers 52, 54.

The elastic portion of the medical article 50 of FIG. 1 is illustrated by way of example only as including a plurality of individual, substantially parallel elastic strands 61 that extend in the MD and are spaced apart in the CMD, such that the elastic portion of FIG. 1 is continuous in the MD and discontinuous in the CMD. In some embodiments, as shown, the strands 61 can be equally spaced apart in the CMD, as shown, or can be spaced apart varying distances, etc.

This particular arrangement of elastic strands 61 and viscoelastic strands 60 is shown by way of example only, and it should be understood that a variety of other arrangements and configurations are possible. For example, in some embodiments, the medical article 50 (e.g., the viscoelastic layer 56) can also include elastic strands 61 that extend in the CMD and are spaced apart in the MD. Furthermore, other non-alternating arrangements of the viscoelastic strands 60 and the elastic strands 61 are possible (e.g., some openings 58 can include more than one elastic strands 61 or no elastic strands 61). In addition, the viscoelastic strands 60 are shown as being substantially the same width (i.e., in the CMD) as the elastic strands 61, but this need not be the case. Moreover, in embodiments in which the medical article 50 includes a separate elastic layer, the elastic layer can include discrete elements, such as the elastic strands 61, or connected structures, such as those shown in FIGS. 2 and 3.

Elastic materials that can be employed in medical articles of the present disclosure can include, but are not limited to, polyurethane-polyurea co-polymers, such as Spandex (or elastane), other suitable elastic materials, or a combination thereof.

Additional exemplary embodiments of viscoelastic layers and medical articles of the present disclosure will now be described with respect to FIGS. 2-4. FIGS. 2-4 illustrate various viscoelastic layers and medical article configurations of the present disclosure, wherein like numerals represent like elements. The viscoelastic layers of FIGS. 2-4 share many of the same elements, features, and functions as the viscoelastic layer 56 described above with respect to FIG. 1. The medical article of FIG. 4 shares many of the same elements, features, and functions as the medical article 50 of FIG. 1. Reference is made to the description above accompanying FIG. 1 for a more complete description of the features and elements (and alternatives to such features and elements) of the embodiments illustrated in FIGS. 2-4. Any of the features described above with respect to FIG. 1 can be applied to the embodiments of FIGS. 2-4, and vice versa.

FIG. 2 illustrates a viscoelastic layer 156 according to another embodiment of the present disclosure that can be employed in medical articles of the present disclosure. The viscoelastic layer 156 generally includes a lattice configuration comprising a plurality of interconnected strands 160 that intersect at intersection sites 162 to define openings 158 that extend through the viscoelastic layer 156 in the z-direction, such that the viscoelastic layer 156 is discontinuous in the MD and the CMD (even though the viscoelastic layer 156 remains connected in the MD and the CMD).

While the strands 160 are shown as extending substantially in both the MD and the CMD, it should be understood that the strands 160 could instead extend at a non-zero and non-right angle with respect to the MD and/or the CMD, and that the orientation of the lattice configuration and the openings 158 within the plane of the MD and the CMD is shown by way of example only.

In addition, the lattice configuration of the viscoelastic layer 156 is shown by way of example only as being generally uniform, such that the strands 160 are spaced a uniform distance apart in the MD and the CMD, and such that the openings 158 are all of about the same size and shape. However, it should be understood that this need not be the case, and instead, the strands 160 could be separated non-uniform distances in the MD and/or the CMD, and the openings 158 could be of non-uniform shapes and sizes.

Furthermore, by way of example only, the strands 160 are each shown as being of substantially the same width. However, this need not be the case, and in some embodiments, at least some of the strands 160 could be much wider than others, or the strands 160 can be of varying or random sizes (i.e., widths).

FIG. 3 illustrates a viscoelastic layer 256 according to another embodiment of the present disclosure that can be employed in medical articles of the present disclosure. The viscoelastic layer 256 includes a web (or sheet or film) 265 that extends in the MD and the CMD and includes a plurality of openings 258 (e.g., die-cut, punched, perforated, or the like) that extend through the web 265 in the z-direction oriented orthogonally with respect to the MD and the CMD.

By way of example only, the openings 258 are shown as being non-uniform in size but as being all circular in shape. However, it should be understood that the openings 258 can have any shape desired (e.g., square, rectangle, triangular, polygonal, etc.), and can instead be uniform in size. In addition, the openings 258 are shown as being somewhat randomly arranged in the web 265; however, it should be understood that the openings 258 can instead be more regularly arranged, e.g., in the MD and/or the CMD, or at a non-zero and non-right angle with respect to the MD and/or the CMD.

Furthermore, by way of example only, the openings 258 are each shown as being fully contained within the web 265; however, it should be understood that this need not be the case, and instead, at least one of the openings 258 can extend through an edge of the web 265.

As with the viscoelastic layer 56 of FIG. 1, in some embodiments, the viscoelastic layer 156 of FIG. 2 and/or the viscoelastic layer 256 of FIG. 3 can include an elastic portion, such as the elastic strands 61 shown in FIG. 1.

FIG. 4 illustrates a medical article 350 according to another embodiment of the present disclosure. The medical article 350 includes one or more support layers 352 and a viscoelastic layer 356. By way of example only, the viscoelastic layer 356 is illustrated as including a lattice network configuration of strands 360, similar to the viscoelastic layer 156 of FIG. 2. However, it should be understood that the medical article 350 can instead include any other viscoelastic layer of the present disclosure.

The medical article 350 is shown in a rolled form or configuration (or provided as a roll), with the medical article 350 being wound around a core 375. As described in greater detail below, in some embodiments, the medical article 350 can be elongated to a desired stretch ratio and rolled up (i.e., about the core 375) while stretched, such that it maintains its stretch ratio.

Similar to the medical article 50 of FIG. 1, the medical article 350 of FIG. 4 can also include an elastic portion, either as a portion of the viscoelastic layer 356, or as one or more separate layers.

Each embodiment shown FIGS. 1-4 is illustrated as a separate embodiment for clarity in illustrating a variety of features of the viscoelastic layers of the present disclosure. However, it should be understood that any combination of elements and features of any of the embodiments illustrated in FIGS. 1-4 and described herein can be employed in the viscoelastic layers and medical articles of the present disclosure.

In some embodiments, medical articles of the present disclosure can form a portion of a compression bandage system. In such embodiments, the medical articles of the present disclosure can, for example, form at least a portion of an inner compression bandage, an outer compression bandage, or both. In addition, or alternatively, the medical articles of the present disclosure can be used in combination with other articles (e.g., bandages) to form the bandage system.

In use, medical articles of the present disclosure (e.g., the medical article 50 of FIG. 1) can be wrapped around a body part (e.g. a limb, torso, head, neck, or a combination thereof) of a subject, such that at least one of the MD and the CMD extends around the body part (e.g., about the circumference of the body part). At a certain point in time during use or wearing of the medical article, a first (e.g., higher/faster) strain rate $S_1$ can be applied the MD and/or the CMD of the medical article, e.g., when the subject walks, runs, or otherwise produces a higher strain rate on the medical article that is wrapped about the body part. The medical article can exhibit a first tensile stiffness $T_1$ at (or in response to) the first strain rate $S_1$. At another point in time during use of the medical article, a second strain rate $S_2$ can be applied in at least one of the MD and the CMD to the medical article wrapped on the body part (e.g., by allowing the subject to stand (e.g., if the medical article is wrapped around the lower leg), to sit (e.g., if the medical article is wrapped around a knee that is bent in the sitting position), or otherwise produce a lower strain rate on the medical article. The medical article can exhibit a second tensile stiffness $T_2$ at (or in response to) the second strain rate $S_2$. In generally, the ratio of $S_1/S_2$ can be at least 100, and the ratio of $T_1/T_2$ can be at least 1.5 in medical articles of the present disclosure.

The rate-dependent characteristics of the medical articles of the present disclosure enable novel methods of applying the medical article. The specific characteristic of the medical article of the present disclosure is that its unconstrained strain recovery is slow compared to similar articles comprising only elastomers with less strain-rate dependence.

As mentioned above, the medical article of the present disclosure can be elongated to a desired stretch ratio and rolled up (e.g., as shown in FIG. 4) while stretched such that it maintains its stretch ratio. To avoid self-adherence and difficulty in unwinding, the medical article can further include an agent to reduce self-adhesion of the medical article (e.g., of one or more support layers). For example, the medical article may be wound with a chemical coating on its inner surface that reduces or eliminates self-adherence. Additionally, or alternatively, an additional non-adherent layer may be wound with the medical article. Then, the article can be unrolled directly onto the body part of a subject with negligible application of tension as the bandage is unrolled. With time, the medical article will begin to recover and apply the amount of pressure to the subject that is determined by the stretch ratio applied to the article before it was rolled.

This method would be impossible with a conventional, strain-rate-independent bandage because the bandage would immediately recover upon unrolling, so it would either lose its stretch or would have to be applied with noticeable tension. Because the medical articles of the present disclosure can be applied with negligible tension and still maintain the correct strain ratio, it can properly be applied by a less-skilled caregiver.

In some embodiments, the medical articles of the present disclosure can be pre-stretched to a stretch ratio of at least 110%, in some embodiments, at least 120%, and in some embodiments, at least 130%.

The embodiments described above and illustrated in the figures are presented by way of example only and are not intended as a limitation upon the concepts and principles of the present disclosure. As such, it will be appreciated by one having ordinary skill in the art that various changes in the elements and their configuration and arrangement are possible without departing from the spirit and scope of the present disclosure.

All references and publications cited herein are expressly incorporated herein by reference in their entirety into this disclosure.

The following embodiments are intended to be illustrative of the present disclosure and not limiting.

EMBODIMENTS

Embodiment 1 is a medical article comprising:
a machine direction (MD) and a cross-machine direction (CMD);
a support layer;
a viscoelastic layer coupled to the support layer, wherein the viscoelastic layer is discontinuous in at least one of the MD and the CMD, wherein the viscoelastic layer recovers, in at least one of the MD and the CMD, at least 70% of its deformation after 48 hours at room temperature after being strained to 50% elongation, such that the medical article has, at room temperature, in at least one of the MD and the CMD, a first tensile stiffness $T_1$ at a first strain rate $S_1$ applied in the at least one of the MD and the CMD and a second tensile stiffness $T_2$ at a second strain rate $S_2$ applied in the at least one of the MD and the CMD, wherein the ratio of $S_1/S_2$ is at least 100, and wherein the ratio of $T_1/T_2$ is at least 1.5.

Embodiment 2 is a method of using a medical article, the method comprising:
providing a medical article comprising
a machine direction (MD) and a cross-machine direction (CMD);
a support layer;
a viscoelastic layer coupled to the support layer, wherein the viscoelastic layer is discontinuous in at least one of the MD and the CMD, wherein the viscoelastic layer recovers, in at least one of the MD and the CMD, at least 70% of its deformation after 48 hours at room temperature after being strained to 50% elongation;
wrapping the medical article around a body part of a subject, such that at least one of the MD and the CMD extends around the body part;
applying a first strain rate $S_1$ in at least one of the MD and the CMD to the medical article wrapped on the body part, wherein the medical article exhibits a first tensile stiffness $T_1$ at the first strain rate $S_1$; and
applying a second strain rate $S_2$ in at least one of the MD and the CMD to the medical article wrapped on the body part, wherein the medical article exhibits a second tensile stiffness $T_2$ at the second strain rate $S_2$;
wherein the ratio of $S_1/S_2$ is at least 100, and wherein the ratio of $T_1/T_2$ is at least 1.5.

Embodiment 3 is the medical article of embodiment 1 or the method of embodiment 2, wherein the ratio of $T_1/T_2$ is at least 2.

Embodiment 4 is the medical article of embodiment 1 or 3 or the method of embodiment 2 or 3, wherein the viscoelastic layer has, in at least one of the MD and the CMD, a first tensile stiffness $V_1$ at a first strain rate $S_1$ applied in at least one of the MD and the CMD and a second tensile stiffness $V_2$ at a second strain rate $S_2$ applied in at least one of the MD and the CMD, wherein the ratio of $S_1/S_2$ is at least 100, and wherein the ratio of $V_1/V_2$ is at least 1.5.

Embodiment 5 is the medical article of any of embodiments 1 and 3-4 or the method of any of embodiments 2-4, wherein the first strain rate is no greater than about 100 cm/min.

Embodiment 6 is the medical article of any of embodiments 1 and 3-5 or the method of any of embodiments 2-5, wherein the second strain rate is at least about 0.5 cm/min.

Embodiment 7 is the medical article of any of embodiments 1 and 3-6 or the method of any of embodiments 2-6, wherein the viscoelastic layer recovers, in at least one of the MD and the CMD, at least 80% strain after 48 hours at room temperature after being strained to 50% elongation.

Embodiment 8 is the medical article of any of embodiments 1 and 3-7 or the method of any of embodiments 2-7, wherein the viscoelastic layer recovers, in at least one of the MD and the CMD, at least 50% strain after 30 minutes at room temperature after being strained to 50% elongation.

Embodiment 9 is the medical article of any of embodiments 1 and 3-8 or the method of any of embodiments 2-8, wherein the medical article forms at least a portion of a self-adhering bandage.

Embodiment 10 is the medical article of any of embodiments 1 and 3-9 or the method of any of embodiments 2-9, wherein the viscoelastic layer includes a plurality of viscoelastic elements extending in the MD and spaced apart in the CMD, such that the viscoelastic layer is discontinuous in the CMD.

Embodiment 11 is the medical article of any of embodiments 1 and 3-10 or the method of any of embodiments 2-10, wherein the viscoelastic layer includes a lattice network configuration, such that the viscoelastic layer is discontinuous in the MD and the CMD.

Embodiment 12 is the medical article of any of embodiments 1 and 3-11 or the method of any of embodiments 2-11, wherein the viscoelastic layer includes a web that extends in the MD and the CMD and includes a plurality of openings that extend through the web in a z-direction oriented orthogonally with respect to the MD and the CMD.

Embodiment 13 is the medical article of any of embodiments 1 and 3-12 or the method of any of embodiments 2-12, wherein the viscoelastic layer has a first dimension in the MD, a second dimension in the CMD, and a third dimension in a z-direction oriented orthogonally with respect to MD and the CMD, and wherein the ratio of the third dimension to the first dimension or the second dimension is no greater than 0.001.

Embodiment 14 is the medical article of any of embodiments 1 and 3-13 or the method of any of embodiments 2-13, wherein the viscoelastic layer is formed of a solid material that excludes air.

Embodiment 15 is the medical article of any of embodiments 1 and 3-14 or the method of any of embodiments 2-14, wherein the support layer is a first support layer, and further comprising a second support layer, wherein the viscoelastic layer is positioned between the first support layer and the second support layer and coupled to both the first support layer and the second support layer.

Embodiment 16 is the medical article or method of embodiment 15, wherein the first support layer and the second support layer are coupled to one another in at least one region where the viscoelastic layer is discontinuous.

Embodiment 17 is the medical article of any of embodiments 1 and 3-16 or the method of any of embodiments 2-16, wherein the medical article further comprises an elastic portion.

Embodiment 18 is the medical article or method of embodiment 17, wherein viscoelastic layer includes the elastic portion.

Embodiment 19 is the medical article or method of embodiment 17 or 18, further comprising an elastic layer that includes at least part of the elastic portion.

Embodiment 20 is the medical article or method of any of embodiments 17-19, wherein the elastic portion includes a plurality of elastic elements extending in the MD and spaced apart in the CMD, such that the elastic portion is discontinuous in the CMD.

Embodiment 21 is the medical article of any of embodiments 1 and 3-20 or the method of any of embodiments 2-20, wherein the medical article is provided in a roll.

Embodiment 22 is the medical article or method of embodiment 21, wherein the medical article is provided in the roll in a stretched state.

Embodiment 23 is the medical article or method of embodiment 21 or 22, wherein the medical article in the roll is in a stretched state, to a stretch ratio of at least 110%.

Embodiment 24 is the medical article or method of any of embodiments 21-23, further comprising at least one of:
a chemical coating applied to the support layer to reduce self-adhesion of the medical article; and
a non-adherent liner positioned adjacent the medical article in the roll.

The following working examples are intended to be illustrative of the present disclosure and not limiting.

EXAMPLES

Materials

Materials utilized in the Examples are shown in Table 1.

TABLE 1

Materials List

| Material | Description | Source |
| --- | --- | --- |
| Spandex Fiber | Opelon 0.7 mm fiber | Beadsmith, Carteret, NJ |
| Cotton Thread | 0.19 mm diameter mercerized cotton thread | Article S970 from Coats and Clark, Greenville, SC |
| Coban ™ | Compression layer from Coban 2 layer Compression System, 10 cm wide | 3M, St. Paul, MN |
| Coban ™ Lite | Compression Layer from Coban 2 Layer Lite Compression System, 10 cm wide | 3M, St. Paul, MN |
| Comprilan ™ | 100% cotton short stretch laminate, 8 cm wide, #01027-00 | BSN Medical, Inc., Rutherford College, NC |
| Fomrez 44-111 | Poly(butylene adipate) Polyol | Chemtura Corporation, Middlebury, CT |
| Glycerol | Ultrapure HPLC grade, #38988 | Alfa Aesar, Ward Hill, MA |
| DBTDL | Di-n-butyltin dilaurate, 95%, #71130 | Alfa Aesar, Ward Hill, MA |
| Desmodur-W | Bis(4-isocyanatocyclohexyl) methane | Bayer MaterialScience, Pittsburgh, PA |
| KFlex 188 | Aliphatic polyester polyol | King Industries, Norwalk, CT |
| Polyester Tape | Polyester Silicone Adhesive Tape 8403, 2.54 cm wide | 3M, St. Paul, MN |

Test Methods

Various tests were conducted to compare base materials (e.g., viscoelastic layers of the present disclosure and comparative materials), and these test methods are referred to as "strand" tests. Additional tests were conducted to compare composite materials comprising the base materials (e.g., medical articles of the present disclosure comprising the viscoelastic layers of the present disclosure and comparative articles), and these test methods are referred to as "laminate" tests.

Strand Tensile

Strands were cut to 10 cm long. A piece of polyester tape was wrapped around each end to produce two 2.5 cm×2.5 cm tabs, separated by 5.1 cm. Ink marks were placed at each end of the 5.1 cm gauge length. The tabs on each end of the strand were loaded into pneumatic grips of a Sintech load frame (MTS Systems, Eden Prairie, Minn.) equipped with 5.1 kg capacity load cell. The initial grip separation was 5.1 cm and the temperature was 24° C. (+/−1° C.). The grips were then separated at a rate of either 51 cm/min (i.e., a first strain rate) or 0.51 cm/min (i.e., a second strain rate). The slope of the initial linear section of the stress/strain curves for each test was reported as the tensile modulus at each separation rate. Three replicate tests were done at each rate for each sample, and the average values reported.

Cotton thread and Spandex fibers were tested as comparatives.

Strand Stress Relaxation

Strands were cut to 46 cm long. A piece of polyester tape was wrapped around each end to produce two 2.5 cm×2.5 cm tabs, separated by 41 cm. Ink marks were placed at each end of the 40 cm gauge length. The tabs on each end of the strand were loaded into pneumatic grips of a Sintech load frame (MTS Systems, Eden Prairie, Minn.) with an initial grip separation of 40 cm. The grips were then separated at a rate of 51 cm/min until a displacement of 20 cm was reached. The load was then monitored for 30 minutes and the percent decrease in stress between the start of the test and after 30 minutes of relaxation time was calculated. After the samples were unloaded from the grips, the strain was allowed to recover at 24° C. (+/−1° C.) for 48 hours. Based on the recovered length of the sample and strain imparted during the stress relaxation test, the strain recovery ratio was calculated. Three replicate tests were done for each sample, and the average values for stress relaxation and strain recovery reported.

Cotton thread and Spandex fibers were tested as comparatives. Cotton threads were separated at a rate of 25 cm/min until a displacement of 2.0 cm was reached.

Laminate Tensile

A piece of laminate was cut to 10 cm long. The laminate was folded in half lengthwise two times to make a four-ply strip 10 cm long with a width of 2.5 cm or less. The ends of the folded laminate were loaded into grips of a Sintech load frame (MTS Systems, Eden Prairie, Minn.) equipped with 200 pound capacity load cell. The initial grip separation was 5.1 cm and the temperature was 24° C. (+/−1° C.). The grips were then separated at a rate of either 51 cm/min or 0.51 cm/min. The slope of the initial linear section of a plot of tensile force vs. percent elongation was divided by the laminate width to give a tensile stiffness value in terms of force per laminate width. At least three replicate tests were done at each rate for each sample, and the average values reported.

Three commercial compression wraps were tested as Comparatives—Comprilian™, Coban™, and Coban™ Lite.

Laminate Stress Relaxation

A piece of laminate was cut to 46 cm long. The laminate was folded in half lengthwise two times to make a four-ply strip 46 cm long with a width of 2.5 cm or less. The ends of the folded laminate were loaded into grips of a Sintech load frame (MTS Systems, Eden Prairie, Minn.) equipped with 91 kg capacity load cell. The initial grip separation was 41 cm and the temperature was 24° C. (+/−1° C.). Ink marks were placed at each end of the 41 cm gauge length. The grips were then separated at a rate of 51 cm/min until a displacement of 20 cm was reached. Example-1 was also tested with a separation rate of 51 cm/min until a displacement of 10 cm was reached. The load was then monitored for 30 minutes, and the percent decrease in load between the start of the test and after 30 minutes of relaxation time was calculated. After the samples were unloaded from the grips, the strain was allowed to recover at 24° C. (+/−1° C.) for more than 48 hours. Based on the recovered length of the sample and strain imparted during the stress relaxation test, the strain recovery ratio was calculated. Three replicate tests were done for each sample.

Comprilian™ and Coban™ compression wraps were tested as Comparatives.

Force Amplitude Modeling

The materials from Viscoelastic-1 and Viscoelastic-2 were characterized using a Q800 dynamic mechanical analyzer (TA Instruments, New Castle, Del.) in tensile mode at 30° C. to model the dynamic performance in a compression laminate application. The test protocol applied a baseline tensile stress to the material, which was intended to model the stress in the material while applying a resting pressure to a limb. After 15 second intervals, the stress was increased by a factor of two for 1.2 seconds to model the increased stress in the material that would correspond to a muscle contraction. The applied stress was then decreased to the baseline stress for 15 seconds before another 2× stress was applied. This sequence was repeated for at least 16 cycles. The baseline stress and the baseline elongation were reported as well as the peak stress and the elongation of the sample 0.4 seconds after the peak stress was applied. The percent increase of the ratio of the 0.4 second peak elongation to the baseline elongation was also reported as the elongation ratio.

A strip of Coban™ Lite compression layer 6.1 mm wide (cut in the down-web direction) was also tested as a Comparative.

Leg Compression

A healthy subject was used to test the elastic behavior of Example-1 and a Comparative compression wrap (Coban™ Lite). The subject's leg measured 20 cm in circumference above the ankle and 37 cm circumference around the calf. Micropore™ tape (3M, St. Paul, Minn.) was used to attached one pressure sensor (MicroLab Elettronica, San Nicolo, Italy) to the B1 position (where the Achilles tendon changes to the calf muscle) and one to the C position (dorsal of the calf, at maximum circumference). The sensors were connected to a pressure reading unit (M-700, MicroLab Elettronica, San Nicolo, Italy).

The leg was then wrapped with the comfort layer from a 3M Coban™ Lite compression wrap. Wrapping was done with minimal overlap of the comfort layer, with enough tension that the wrap was uniform, wrinkle free, and did not slip. The measured pressure from the comfort layer was approximately 15 mm Hg at the B1 location.

Example-1 was pre-stretched to approximately 25% elongation and then applied over the comfort layer with approximately 50% overlap.

The sub-bandage pressure was then measured with the leg in both a supine and standing position, initially (after short loading by a 1-minute walk immediately after wrapping) and after 20 minutes of standing. The Static Stiffness Index (SSI) was also calculated as the difference between the standing and supine pressures. Additionally, the amplitude (maximum pressure reading minus minimum pressure reading) was measured during walking.

Pressure Test on Roll Winder

A 5-cm cylinder of polyoxymethylene was designed in such a way that it could be fit with fluid bags and sensor tubing, without measureable effect on the final radius (shape) of the cylinder. A 65 mm×65 mm fluid bag was made of 0.25 mm thick PVC-foil, and filled with 11 grams glycol. The maximum thickness of the filled bag was 2.5 mm. The weight of the bag was approximately 16 grams. Two-sided adhesive tape (467 MP, 3M Company, St. Paul, Minn.) was used to attach a small (approximately 33 mm×30 mm) Kikuhime sensor (MediTrade, Soro, Denmark) to the inside of the test cylinder. The sensor was connected to a Kikuhime pressure monitor of same supplier. A fluid bag was positioned on top of the Kikuhime sensor so that the bag filled the entire indented area of the test cylinder. The Kikuhime sensor and the fluid bag were not fixed to each other. Because of form fit, the fluid bag stayed almost in position, but was additionally secured with tape at two adjacent edges (running in circumferential direction of the cylinder). On top of the fluid bag, a PicoPress sensor was positioned and fixed with double-sided adhesive tape and connected to a PicoPress pressure monitor. The tube was conducted through the designated channel in the cylinder and was secured with tape. Via a 3-way luer lock stopcock, the Kikuhime pressure monitor, Kikuhime sensor, and a pressure sphygmomanometer were connected with each other.

The cylinder was fit in an automated roller, which rotated the cylinder in a controlled manner with thirteen turns per minute. One end of a 10 cm wide and 50 cm long stripe of Coban™ 2 comfort layer was attached on the cylinder with tape, opposite of the center of the fluid bag. A load was clamped to the free end of the Coban™ wrap. The weight of clamp and load was 300 grams. One complete circular winding was applied by automated roller. Once wrapped, the wrap was secured to the automated roller and the excess cut off.

One end of a 10-cm wide and 70-cm long strip of Example-1 was attached to the cylinder with tape, again starting exactly on the opposite of the center of the fluid bag. Prior to winding, the material was stretched to 20% (within 1 min.) and was then loaded with a 750 g load to avoid shrinkage during winding. Two complete circular windings were applied (automated winding), the elastic was secured to the automated roller, and the excess cut off.

To simulate the standing position, the Kikuhime sensor was inflated to 100 mmHg, causing the sensor to expand in volume. To simulate the lying (supine) position, the Kikuhime sensor was evacuated. The "strain index" is the difference of the pressure measured in the inflated state and the pressure measured in the evacuated state, both measured with the PicoPress equipment.

The following test sequence was utilized:
The first pressure measurement was done without inflating the Kikuhime sensor 30 seconds after the winding.
6 minutes later, the Kikuhime sensor was inflated.
3 minutes later, the Kikuhime sensor was evacuated again.
10 minutes later, the Kikuhime sensor was inflated again. Hold for 90 minutes.
After the 90-min hold, the Kikuhime sensor was evacuated.

EXAMPLES

Visco Elastic-1

Figure 5:
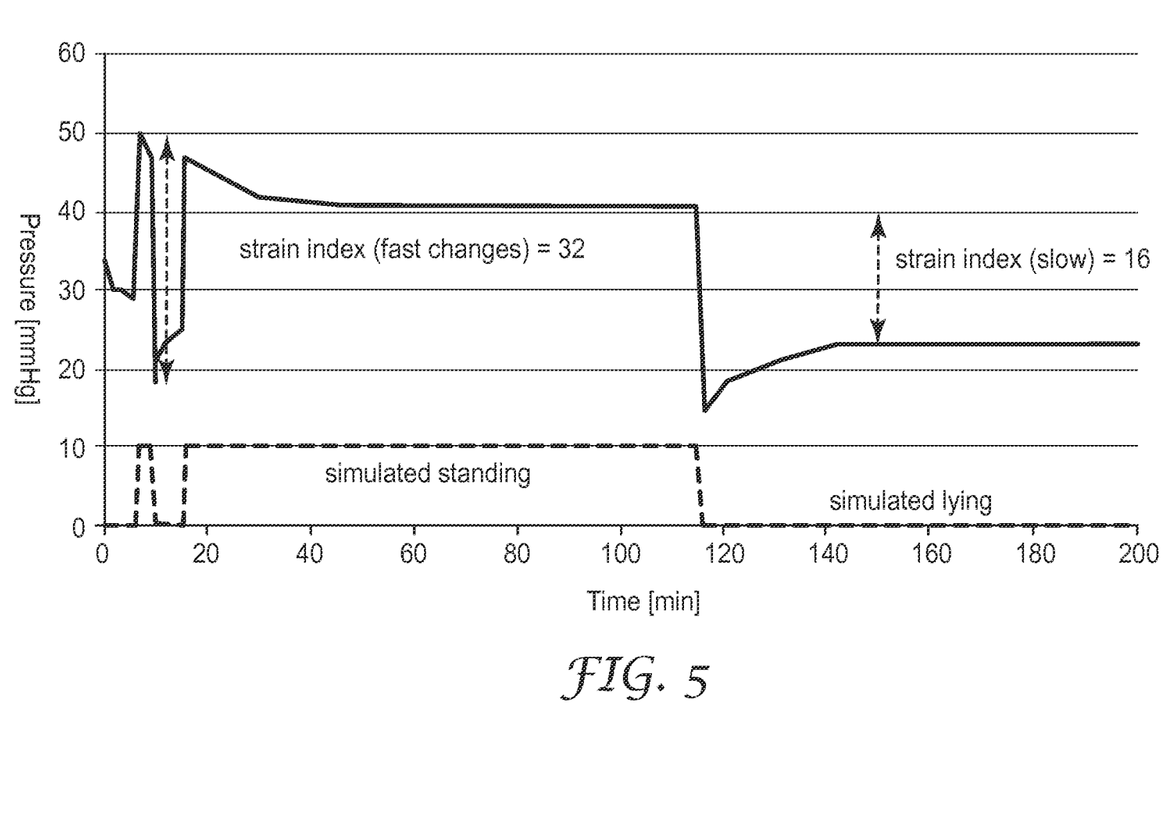
FIG. 5 is a graph of pressure measurements on a roll winder, as set forth in the Examples.

Viscoelastic-1 was prepared using the coating apparatus as generally shown in FIG. 5 of US patent application 2011/0045306. The notched bar was heated using circulating fluid at 49° C. Forming webs (30 cm wide) were used as both the top and bottom liners. The films were coated at a line speed of 1.5 m/min with a mixture of 0.712 parts Desmodur N3300, 1.0 part KFlex 188, and 0.0012 parts DBTDL. The heated platen contained 5 zones, each 1.2 m long. The temperature of the first 4 zones was set to 82.2° C. while the last zone was at room temperature. The unwind tension for the top and bottom liners, and the rewind tension for the resultant coated film were all set to 89 N. The gap between the two liners at the nip formed by the notched bar and the flatbed was set to 0.1 mm. The resulting film was 0.11 mm thick and was slit down to strands 1.1 mm wide.

Viscoelastic-2

Strips of material were derived from a polyurethane film prepared by reactive extrusion. The film was formed from a mixture of Fomrez 44-111 (44.4 wt %), 1,4-butanediol (10.4 wt %), glycerol (0.2%), DBTDL (0.08%), and Desmodur-W (45 wt %) and was 0.13 mm thick. The film was then slit to produce 1.1 mm wide strands.

Example-1

Nonwoven Web-A 11 gsm (grams/m²) nonwoven web was made by bonding carded polyester fibers (1.5 denier, 3.8 cm length) with an acrylic binder solution. The fiber to binder ratio was approximately 75:25.

A series of 40 Viscoelastic-1 strands were spaced 0.5 cm apart and were stretched to 25% elongation. In the stretched state, these strands were laminated between two Nonwoven Webs as described in U.S. Pat. No. 3,575,782. The resulting laminate was slit to a 10 cm width. This laminate was subsequently impregnated to a coating weight between 40 and 75 g/m2, as described in U.S. Pat. No. 7,854,717, "Preparation of Self Adhering Compression Bandages for Use as an Outer Bandage".

Example-2

Example-2 was prepared as described in Example-1 using Viscoelastic-2, and stretching to 50% elongation.

Results

TABLE 1

Strand Tensile Test Results

| Material | E' (MPa) | | |
|---|---|---|---|
| | 51 cm/min | 0.51 cm/min | Ratio |
| Viscoelastic-1 | 1000 | 480 | 2.1 |
| Viscoelastic-2 | 190 | 57 | 3.3 |
| Spandex Fiber | 3.9 | 4.1 | 0.95 |
| Cotton Thread | 7100 | 5600 | 1.3 |

TABLE 2

Strand Stress Relaxation Results

| Material | Elongation | Stress Relaxation after 30 min | Strain Recovery after 48 hrs |
|---|---|---|---|
| Viscoelastic-1 | 50% | 63% | 100% |
| Viscoelastic-2 | 50% | 59% | 100% |
| Spandex Fiber | 50% | 8% | 100% |
| Cotton Thread | 50% | Thread broke | Thread broke |
| Cotton Thread | 5% | 71% | 69% |

TABLE 3

Laminate Tensile

| Material | Tensile Stiffness (N/cm) | | |
|---|---|---|---|
| | 1000%/min | 10%/min | Ratio |
| Example-1 | 20.6 | 8.0 | 2.57 |
| Example-2 | 10.9 | 4.0 | 2.71 |
| Comprilan ™ | 0.35 | 0.39 | 0.92 |
| Coban ™ | 0.66 | 0.60 | 1.11 |
| Coban ™ Lite | 0.34 | 0.32 | 1.05 |

TABLE 4

Laminate Stress Relaxation

| Material | Elongation | Stress Relaxation after 30 min | Strain Recovery after 48 hrs |
|---|---|---|---|
| Example-1 | 50% | Laminate broke | Laminate broke |
| Example-1[a] | 25% | 60% | 97% |
| Example-2 | 50% | 63% | 99% |
| Comprilan ™ | 50% | 35% | 99% |
| Coban ™ | 50% | 43% | 100% |

[a]Average of two replicates

TABLE 5

Force Amplitude Modeling

| Material | Baseline Tensile Stress (MPa) | Baseline Elongation | Peak Stress (MPa) | Elongation After 0.4 Seconds of Peak Stress | Elongation Ratio |
|---|---|---|---|---|---|
| Viscoelastic-1[a] | 0.77 | 24% | 1.54 | 26% | 8% |
| Viscoelastic-1[a] | 1.6 | 75% | 3.2 | 81% | 8% |
| Viscoelastic-2[b] | 3.7 | 91% | 7.4 | 95% | 4% |
| Coban ™ Lite | 0.025 | 41% | 0.05 | 51% | 24% |
| Coban ™ Lite | 0.049 | 58% | 0.098 | 63% | 9% |

[a]Strands were 0.22 mm thick and 2.5 mm wide
[b]Strands were 0.14 mm thick and 3.9 mm wide For a purely linear-elastic material, doubling the stress would be expected to approximately double the elongation, so elongation ratios of less than 100% indicate the desired non-linear-elastic behavior, with smaller ratios being more desirable. For the comparative example with Coban™ Lite, the strain increase was very low when the material was at a full stretch value of 58% elongation, but at a lower elongation of only 41%, the strain increase was higher. In contrast, Viscoelastic-1 and Viscoelastic-2 showed very low strain increases even without the presence of laminated cover webs, and this low strain increase is shown with Viscoelastic-1 to be nearly insensitive to the degree of elongation. The low increases in strain with large increases in stress that were observed for Viscoelastic-1 and Viscoelastic-2 demonstrate the viscoelastic character of these materials that is desirable for use as components in a compression laminate.

TABLE 6

Leg Pressure Measurements

| | B1 (mm Hg) | | | C (mm Hg) | | |
|---|---|---|---|---|---|---|
| Material | Supine[a] | Standing[b] | SSI | Supine[a] | Standing[b] | SSI |
| Example-1 | 44 | 74 | 30 | 43 | 58 | 15 |
| Walking, Amplitude[a] | 35 | 123 | 88 | 42 | 53 | 11 |
| After 20 min standing | 42 | 73 | 31 | 35 | 52 | 17 |
| Comparative (Coban ™ Lite) | 25 | 54 | 29 | 35 | 55 | 20 |
| Walking, Amplitude[a] | 21 | 66 | 45 | 35 | 46 | 11 |
| After 20 min standing | 19 | 50 | 31 | 28 | 49 | 21 |

[a]lower amplitude value
[b]higher amplitude value

As shown in Table 6, the supine pressure after 20 minutes standing, does not drop more than in the Comparative Coban™ Lite wrap. As desired, in case of the experimental material, the walking amplitude at B1 is almost twice as high as with the Coban™ wrap.

Pressure Test on Roll Winder

FIG. 3 demonstrates that a quick sequence in inflating and evacuating the Kikuhime sensor, which corresponds to quick volume changes, causes peak differences in the pressure readings of 32 mmHg with the PicoPress sensor. The pressure difference of both states, the "strain index", after waiting 30 minutes, i.e. after the transient behavior has leveled out, is 16 mmHg. This means that a human leg, which is wrapped with such bandage material like Example-1 will experience larger pressure differences in case of fast leg volume changes—e.g. caused by muscle movements or vein filling due to gravity—compared to the pressure differences measured after remaining in particular states (lying or standing).

Various features and aspects of the present disclosure are set forth in the following claims.

What is claimed is:

1. A medical article comprising:
   a machine direction (MD) and a cross-machine direction (CMD);
   a support layer;
   a viscoelastic layer coupled to the support layer, wherein the viscoelastic layer is discontinuous in at least one of the MD and the CMD, wherein the viscoelastic layer recovers, in at least one of the MD and the CMD, at least 70% of its deformation after 48 hours at room temperature after being strained to 50% elongation, such that the medical article has, at room temperature, in at least one of the MD and the CMD, a first tensile stiffness $T_1$ at a first strain rate $S_1$ applied in the at least one of the MD and the CMD and a second tensile stiffness $T_2$ at a second strain rate $S_2$ applied in the at least one of the MD and the CMD,
   wherein the ratio of $S_1/S_2$ is at least 100,
   wherein S1 is no greater than 500 cm/min, and
   wherein the ration of $T_1/T_2$ is at least 1.5 and no greater than 10.

2. The medical article of claim 1, wherein the medical article further comprises an elastic portion.

3. The medical article of claim 2, wherein viscoelastic layer includes the elastic portion.

4. The medical article of claim 2, further comprising an elastic layer that includes at least part of the elastic portion.

5. The medical article of claim 2, wherein the elastic portion includes a plurality of elastic elements extending in the MD and spaced apart in the CMD, such that the elastic portion is discontinuous in the CMD.

6. The medical article of claim 1, wherein the medical article is provided in a roll.

7. The medical article of claim 6, wherein the medical article in the roll is in a stretched state, to a stretch ratio of at least 110%.

8. The medical article of claim 6, further comprising at least one of:
   a chemical coating applied to the support layer to reduce self-adhesion of the medical article; and
   a non-adherent liner positioned adjacent the medical article in the roll.

9. The medical article of claim 1, wherein the support layer is a first support layer, and further comprising a second support layer, wherein the viscoelastic layer is positioned between the first support layer and the second support layer and coupled to both the first support layer and the second support layer.

10. The medical article of claim 9, wherein the first support layer and the second support layer are coupled to one another in at least one region where the viscoelastic layer is discontinuous.

11. The medical article of claim 1, wherein the ratio of $T_1/T_2$ is at least 2.

12. The medical article of claim 1, wherein the ratio of $T_1/T_2$ is at least 3.

13. The medical article of claim 1, wherein the first strain rate is no greater than about 100 cm/min.

14. The medical article of claim 1, wherein the second strain rate is at least about 0.5 cm/min.

15. The medical article of claim 1, wherein the viscoelastic layer recovers, in at least one of the MD and the CMD, at least 80% strain after 48 hours at room temperature after being strained to 50% elongation.

16. The medical article of claim 1, wherein the viscoelastic layer recovers, in at least one of the MD and the CMD, at least 50% strain after 30 minutes at room temperature after being strained to 50% elongation.

17. The medical article of claim 1, wherein the medical article forms at least a portion of a self-adhering bandage.

18. The medical article of claim 1, wherein the viscoelastic layer includes a plurality of viscoelastic elements extending in the MD and spaced apart in the CMD, such that the viscoelastic layer is discontinuous in the CMD.

19. The medical article of claim 1, wherein the viscoelastic layer includes a lattice network configuration, such that the viscoelastic layer is discontinuous in the MD and the CMD.

20. The medical article of claim 1, wherein the viscoelastic layer includes a web that extends in the MD and the CMD and includes a plurality of openings that extend through the web in a z-direction oriented orthogonally with respect to the MD and the CMD.

21. The medical article of claim 1, wherein the viscoelastic layer has a first dimension in the MD, a second dimension in the CMD, and a third dimension in a z-direction oriented orthogonally with respect to MD and the CMD, and wherein the ratio of the third dimension to the first dimension or the second dimension is no greater than 0.001.

22. The medical article of claim 1, wherein the viscoelastic layer is formed of a solid material that excludes air.

23. A method of using a medical article, the method comprising:
    providing a medical article comprising
        a machine direction (MD) and a cross-machine direction (CMD);
        a support layer;
        a viscoelastic layer coupled to the support layer, wherein the viscoelastic layer is discontinuous in at least one of the MD and the CMD, wherein the viscoelastic layer recovers, in at least one of the MD and the CMD, at least 70% of its deformation after 48 hours at room temperature after being strained to 50% elongation;
    wrapping the medical article around a body part of a subject, such that at least one of the MD and the CMD extends around the body part;
    applying a first strain rate $S_1$ in at least one of the MD and the CMD to the medical article wrapped on the body part, wherein the medical article exhibits a first tensile stiffness $T_1$ at the first strain rate $S_1$; and
    applying a second strain rate $S_2$ in at least one of the MD and the CMD to the medical article wrapped on the body part, wherein the medical article exhibits a second tensile stiffness $T_2$ at the second strain rate $S_2$;
    wherein the ratio of $S_1/S_2$ is at least 100,
    wherein $S_1$ is no greater than 500 cm/min, and
    wherein the ratio of $T_1/T_2$ is at least 1.5 and no greater than 10.

* * * * *

UNITED STATES PATENT AND TRADEMARK OFFICE
CERTIFICATE OF CORRECTION

PATENT NO.         : 10,888,463 B2
APPLICATION NO.    : 15/103898
DATED              : January 12, 2021
INVENTOR(S)        : Joseph Douglas Rule It is certified that error appears in the above-identified patent and that said Letters Patent is hereby corrected as shown below:

In the Claims

Column 22,
Line 27, in Claim 1, delete "ration" and insert -- ratio --, therefor.

Signed and Sealed this
Tenth Day of January, 2023

Katherine Kelly Vidal
*Director of the United States Patent and Trademark Office*